United States Patent [19]

Nagarajan et al.

[11] Patent Number: 5,591,714
[45] Date of Patent: Jan. 7, 1997

[54] DERIVATIVES OF A82846

[75] Inventors: Ramakrishnan Nagarajan; Amelia A. Schabel, both of Indianapolis, Ind.

[73] Assignee: Eli Lilly and Company, Indianapolis, Ind.

[21] Appl. No.: 322,972

[22] Filed: Oct. 13, 1994

Related U.S. Application Data

[63] Continuation of Ser. No. 960,316, Oct. 13, 1992, abandoned, which is a continuation of Ser. No. 449,171, Dec. 13, 1989, abandoned.

[51] Int. Cl.$^6$ .......................... A61K 38/12; A61K 38/14; C07K 9/00
[52] U.S. Cl. ............................ 514/9; 514/8; 530/317; 530/322; 530/323
[58] Field of Search ........................... 530/317, 322, 530/323; 514/8, 9

[56] References Cited

U.S. PATENT DOCUMENTS

| | | | |
|---|---|---|---|
| 4,552,701 | 11/1985 | Nagarajan et al. | 260/112.5 |
| 4,639,433 | 1/1987 | Hunt et al. | 514/8 |
| 4,643,987 | 2/1987 | Nagarajan et al. | 514/8 |
| 4,698,327 | 10/1987 | Nagarajan et al. | 514/8 |
| 4,946,941 | 8/1990 | Kondo et al. | 530/317 |

FOREIGN PATENT DOCUMENTS

| | | |
|---|---|---|
| 0231111 | 8/1987 | European Pat. Off. . |
| 0265071 | 4/1988 | European Pat. Off. . |
| 0276740 | 8/1988 | European Pat. Off. . |
| 0287110 | 10/1988 | European Pat. Off. . |

OTHER PUBLICATIONS

E. N. Olsufyeva et al., *Antibiotics and Chemotherpy*, 34, 352–358 (May 1989).

Centers for Disease Control and Prevention, "Nosocomial Enterococci Resistant to Vancomycin—United States, 1989–1993", MMWR Morbid Mortal Wkly Rep, 42:597–599 (1993).

Richard V. Spera, Jr., and Bruce F. Farber, "Multiply–Resistant Enterococcus Faecium—the Nosocomial Pathogen of the 1990s", JAMA 268(18):2563–2564 (Nov. 11, 1992).

Richard V. Spera, Jr., and Bruce F. Farber, "Multidrug–Resistant Enterococcus Faecium—an Untreatable Nosocomial Pathogen", Drugs 48(5):678–688 (1994).

J. Clin. Microbiol., 26:1216–1218 (1988). "Recovery of Resistant Enterococci during Vancomycin prophylaxis", Kaplan, A. et al.

Antimicrob. Agents Chemother., 33:198–203 (1989). Schlaes et al., "Inducible Transferable Resistance to Vancomycin in Enterococcus faecalis A256".

Ramakrishnan Nagarajan, "Structural Activity Relationships of Vancomycin and Related Antibiotics", 28th Intersci. Conf. Antimicrob. Agents Chemother., Oct. 23–26, 1988.

Kondo et al., Chemical Abstract, vol. 107, No. 196526w (1987).

Hamill et al., Chemical Abstract, vol. 111, No. 76518f (1989).

Leclercq, et al., *N. Engl. J. Med.*, 319, 157–161 (1988).

Assandri, et al., *Eur J Clin Pharmacol*, 33, 191–195 (1987).

Nicas, et al., *Antimicrobial Agents and Chemotherapy*, 33, 1477–1481 (1989).

Wick, et al., *Journal of Bacteriology*, 81, 233–235 (1961).

Moellering, et al., *Reviews of Infectious Diseases*, 3, S230–S235 (1981).

Uttley, et al., *The Lancet*, 1, 57–58 (1988).

Nagarajan, et al., *J. Org. Chem.*, 54, 983–986 (1989).

Nagarajan, et al., *J. of Antibiotics*, 41, 1430–1438 (1988).

Nagarajan, et al., *J. of Antibiotics*, 42, 63–72 (1989).

*Primary Examiner*—Michael P. Woodward
*Assistant Examiner*—Benet Prickril
*Attorney, Agent, or Firm*—Kathleen R. S. Page; Joseph A. Jones; James P. Leeds

[57] ABSTRACT

New N-alkyl and N-acyl derivatives of A82846A, A82846B, A82846C and PA-42867-A are provided. The new glycopeptide derivatives are useful for the treatment of susceptible bacterial infections, especially infections due to Gram-positive microorganisms.

32 Claims, No Drawings

DERIVATIVES OF A82846

This application is a continuation of application Ser. No. 07/960,316, filed on Oct. 13, 1992, which is a continuation of application Ser. No. 07/449,171, filed on Dec. 13, 1989 both now abandoned.

BACKGROUND OF THE INVENTION

New improved antibiotics are continually in demand, particularly for the treatment of human diseases. Increased potency, expanded spectrum of bacterial inhibition, increased in vivo efficacy, and improved pharmaceutical properties are some of the goals for improved antibiotics.

Enterococci are important human pathogens. Infections caused by enterococci are generally difficult to treat. Glycopeptides, such as vancomycin and teicoplanin, have become important therapies in the treatment of infections due to enterococci. However, strains of *E. faecium* and *E. faecalis* have recently been isolated that are resistant to vancomycin. R. Leclercq et al., "Plasmid Mediated Resistance to Vancomycin and Teicoplanin in *Enterococcus Faecium*," *The New England Journal of Medicine*, 319(3), 157–116 (1988) and A. H. C. Uttley et al., "Vancomycin-Resistant Enterococci," *Lancet*, 1, 57–58 (1988). The isolates were also found to be resistant to other antibiotics.

Glycopeptides, such as vancomycin and teicoplanin, exhibit various degrees of serum protein binding. The level of human serum protein binding for vancomycin and teicoplanin has been reported to be 55% and about 90%, respectively. R. Moellering et al., "Pharmacokinetics of Vancomycin in Normal Subjects and in Patients with Reduced Renal Function," *Reviews of Infectious Disease*, 3, (Supp.), S230–S235 (1981) and A. Assandri and A. Bernareggi, "Binding of Teicoplanin to Human Serum Albumin," *Eur. J. Clinical Pharmacol.*, 33, 191–195 (1987). The percentage of serum protein binding exhibited by teicoplanin is considered to be a high level of binding; however, the level of serum protein binding exhibited by vancomycin is relatively low. The free or unbound form of the antibiotic is the form that participates in the biological activity. Therefore, the binding of the antibiotics to serum proteins affects the pharmaceutical properties of the antibiotic.

In the search for new antibiotics, structural modification of known antibiotics is attempted whenever possible. The glycopeptide antibiotics have such complex structures that even small changes are difficult. Furthermore, it is difficult to predict the effect these changes will make in the antimicrobial and physiological properties. Processes for modifying known antibiotics and the new active derivatives made by such processes, therefore, continue to be of great importance.

Previously, N-alkyl and N-acyl derivatives of the glycopeptides vancomycin, A51568A, A51568B, M43A and M43D have been prepared (U.S. Pat. Nos. 4,639,433; 4,643,987; and 4,698,327). Several of these compounds exhibited microbiological activity against vancomycin-resistant isolates. T. Nicas et al., *Antimicrobial Agents and Chemotherapy*, 33(9), 1477–1481 (1989).

The formula I compounds are new members of the glycopeptide group of antibiotics. These new compounds are N-alkyl and N-acyl derivatives of the known A82846 glycopeptides, factors A, B, and C (EPO 265,071 A1), and PA-42867-A (EPO 231,111 A2). Representative formula I compounds exhibited antimicrobial activity against vancomycin-resistant isolates. Also, the new compounds are not as highly serum protein bound as other glycopeptides. The level of serum protein binding for the formula I compounds is similar to that exhibited by vancomycin. This level is much lower than that of other highly potent glycopeptides, such as teicoplanin.

SUMMARY OF THE INVENTION

This invention relates to novel glycopeptide derivatives of formula I:

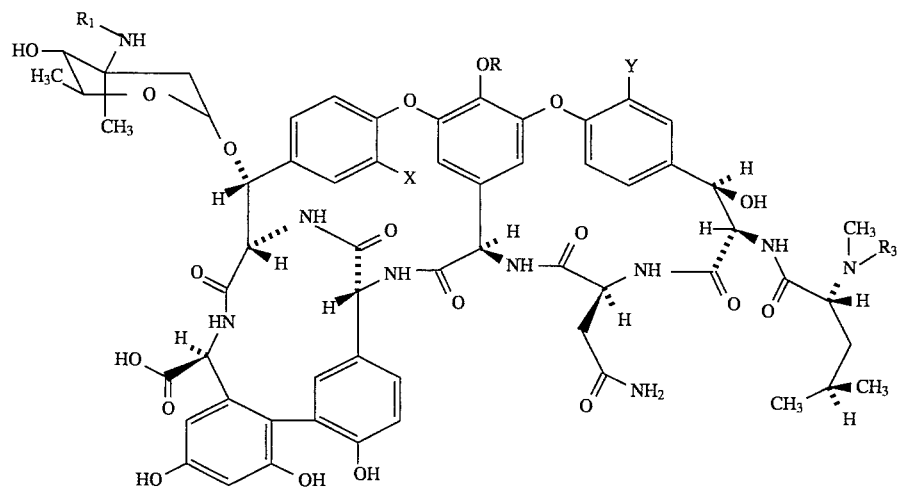

wherein:

R is hydrogen or a (4-epi-vancosaminyl)-O-glucosyl group of formula

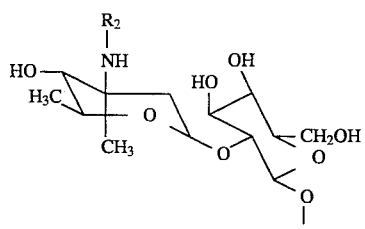

or the glucosyl group of formula

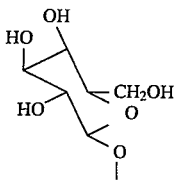

X is hydrogen or chloro;
Y is hydrogen or chloro;
$R_1$, $R_2$, and $R_3$ are independently hydrogen; $C_8$–$C_{12}$ alkyl; $C_2$–$C_9$ alkanoyl; or a group of formula

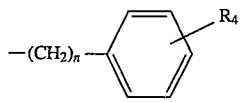

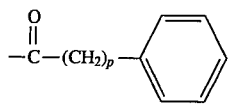

or

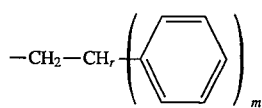

n is 1 to 3;
$R_4$ is hydrogen, halo, $C_1$–$C_8$ alkyl, $C_1$–$C_8$ alkoxy, or a group of formula

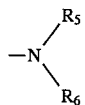

$R_5$ and $R_6$ are independently hydrogen or $C_1$–$C_3$ alkyl;
p is 0 to 2;
m is 2 or 3, and r=3-m;
provided that, where R is a (4-epi-vancosaminyl)-O-glucosyl group, $R_1$, $R_2$, and $R_3$ are not all hydrogen, and where R is hydrogen or a glucosyl group, $R_1$ and $R_3$ are not both hydrogen; or a pharmaceutically acceptable salt thereof.

This invention also relates to compositions for the treatment of susceptible bacterial infections comprising a compound of formula I in combination with an acceptable pharmaceutical carrier. Methods for the treatment of susceptible bacterial infections with compositions of formula I are also a part of this invention.

DETAILED DESCRIPTION OF THE INVENTION

The term "N-alkyl derivative" means a derivative of A82846A, A82846B, A82846C or PA-42867-A wherein a hydrogen atom of one or more of the amino groups is replaced by an alkyl or substituted alkyl group.

The term "N-acyl derivative" means a derivative of A82846A, A82846B, A82846C or PA-42867-A wherein a hydrogen atom of one or more of the amino groups is replaced by an alkanoyl or substituted alkanoyl group.

The term "alkyl" means a $C_1$ to $C_{12}$ straight or branched chain hydrocarbon, e.g., methyl, ethyl, n-propyl, isopropyl, n-butyl, s-butyl, t-butyl, n-pentyl, iso-pentyl, n-hexyl, 2-methylhexyl, 3-methylhexyl, n-heptyl, 2-methylheptyl, n-octyl, 2-methyloctyl, 3-methyloctyl, n-nonyl, 2-methylnonyl, n-decyl, 2-methyldecyl, n-undecyl, 2-methylundecyl, or n-dodecyl. When the term "alkyl" is described as $C_1$ to $C_8$ alkyl, the term means, e.g., methyl, ethyl, n-propyl, isopropyl, n-butyl, s-butyl, t-butyl, n-pentyl, isopentyl, n-hexyl, n-heptyl, or n-octyl. When the term "alkyl" is described as $C_8$ to $C_{12}$ alkyl, the term means, e.g., n-octyl, 2-methyloctyl, 3-methyloctyl, n-nonyl, 2-methylnonyl, n-decyl, n-undecyl, 2-methylundecyl, or n-dodecyl. When the term "alkyl" is described as $C_8$ to $C_{10}$ alkyl, the term means, e.g., n-octyl, 2-methyloctyl, 3-methyloctyl, n-nonyl, 2-methylnonyl, or n-decyl. When the term "alkyl" is described as $C_1$ to $C_3$ alkyl, the term means methyl, ethyl, n-propyl, or isopropyl.

The term "$C_2$ to $C_9$ alkanoyl" means a straight or branched chain $C_1$ to $C_8$ alkyl group, as defined supra, attached to a carbonyl group.

The term "$C_1$ to $C_8$ alkoxy" means a $C_1$ to $C_8$ alkyl group, as defined supra, attached to an oxygen atom. The $C_1$ to $C_8$ alkoxy group includes, for example, methoxy, ethoxy, propoxy, isopropoxy, n-butoxy, s-butoxy, t-butoxy, n-pentoxy, isopentoxy, n-hexyloxy, n-heptyloxy, and n-octyloxy.

The term "halo" means a halogen of the group fluoro, chloro, bromo, and iodo. Preferably, the term "halo" includes fluoro, chloro, and bromo.

The pharmaceutically acceptable addition salts of the formula I compounds are a part of this invention. Pharmaceutically acceptable addition salts are those salts useful in the chemotherapy of a warm-blooded animal, such that the toxicity of the salt form is not greater than that of the non-salt form. The formula I compounds each have a carboxyl group and one or more amino groups which can react to form various salts. The acid addition salts, formed by standard reactions of the formula I compounds with both organic and inorganic acids, are a preferred group of salts. Examples of the pharmaceutically acceptable salts are the salts formed by the reaction of a formula I compound with hydrochloric, succinic, citric, lactic, tartaric, phosphoric, and acetic acid.

The formula I compounds where R is a (4-epi-vancosaminyl)-O-glucosyl group are prepared from the A82846 antibiotics, factors A, B, and C, and from PA-42867-A. The structures of these antibiotics are shown in formula II. The methods for the preparation of A82846A, A82846B, and A82846C are described in European Patent Publication 265,071 A1. The method for the preparation of PA-42867-A is described in European Patent Publication 231,111 A2.

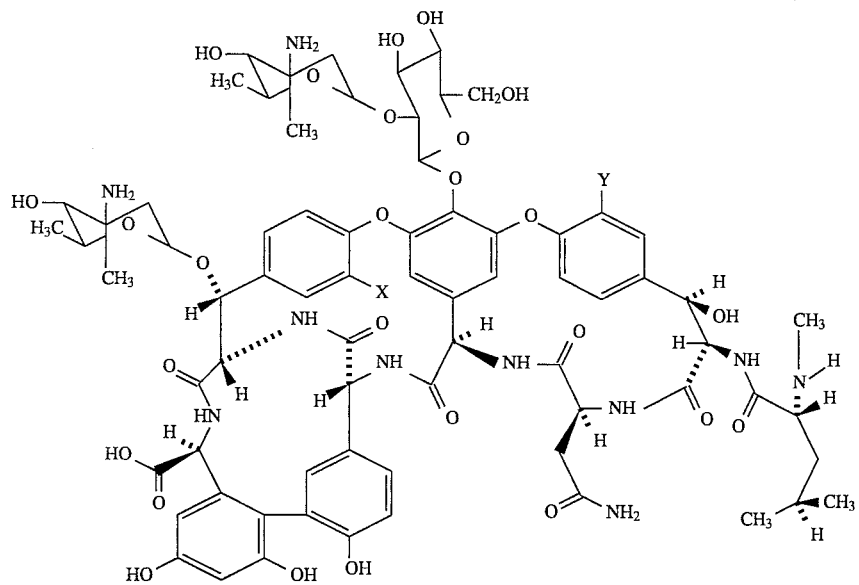

Formula II Compounds

| No. | Compound | X | Y |
|---|---|---|---|
| IIa | A82846A | H | Cl |
| IIb | A82846B | Cl | Cl |
| IIc | A82846C | H | H |
| IId | PA-42867-A | Cl | H |

The formula I compounds where R is hydrogen or the glucosyl group are prepared from the acid hydrolysis products of A82846A, A82846B, A82846C and PA-42867-A. The structures of the acid hydrolysis products are shown in formulas III and IV. The methods for the preparation of the acid hydrolysis products of PA-42867-A, des-(4-epi-vancosaminyl)-PA-42867-A (IIId) and des-(4-epi-vancosaminyl-O-glucosyl)-PA-42867-A (IVd), are described in European Patent Publication 231,111 A2. The des-(4-epi-vancosaminyl) and des-(4-epi-vancosaminyl-O-glucosyl) derivatives of A82846A, B, and C are prepared by treating A82846A, B, or C with trifluoroacetic acid (TFA) at a temperature of about −10° C. to about 80° C. for a period of about 1 to 60 hours (see U.S. Pat. No. 4,552,701 for a description of methods to selectively remove sugar groups from glycopeptide-like antibiotics). Short reaction periods, e.g. 1 to 2 hours, and low temperatures, 0° C., favor the formation of the des-(4-epi-vancosaminyl) derivatives of A82846A, B, and C, formulas IIIa–c.

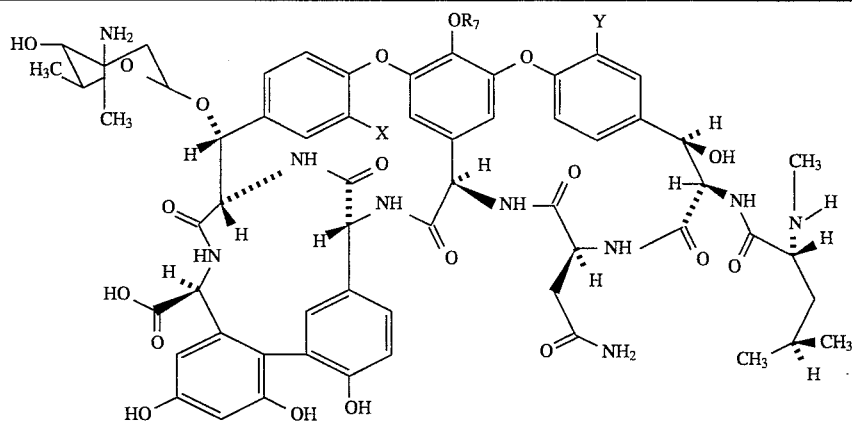

Formula III and IV Compounds

| Compound No. | $R_7$ | X | Y |
|---|---|---|---|
| IIIa | glucosyl | H | Cl |
| IIIb | glucosyl | Cl | Cl |
| IIIc | glucosyl | H | H |

| | | | |
|---|---|---|---|
| IIId | glucosyl | Cl | H |
| IVa | H | H | Cl |
| IVb | H | Cl | Cl |
| IVc | H | H | H |
| IVd | H | Cl | H |

The N-alkyl derivatives of this invention are prepared by the reaction of a formula II, III, or IV compound with an aldehyde to form an intermediate Schiff's base. The reaction is carried out in a polar organic solvent, such as dimethylformamide, or a mixture of polar organic solvents, such as a mixture of dimethylformamide and methanol, at a temperature of about 25° C. to about 100° C. The reaction for the formation of the Schiff's base is preferably carried out at a temperature of from about 60° C. to about 70° C. for 30 minutes to 2 hours in a mixture of dimethylformamide and methanol.

The intermediate Schiff's base is then reduced, preferably without isolation, to produce the N-alkyl derivatives. The reduction of the Schiff's base can be effected using a chemical reducing agent such as a metal borohydride, e.g. sodium borohydride or sodium cyanoborohydride. The reaction can be carried out in a polar organic solvent, such as dimethylformamide, or a mixture of polar organic solvents, such as dimethylformamide and methanol. The reduction can be carried out at a temperature of about 25° C. to about 100° C. for 1 to 5 hours. The reduction is preferably carried out using an excess of sodium cyanoborohydride in a mixture of dimethylformamide and methanol at about 60° C. to about 70° C. for 1 to 2 hours.

The ratio of the aldehyde to the formula II, III, or IV compound and the reaction conditions determines the products of the reaction. The formation of the monoalkylated derivatives is favored by using a slight excess of the aldehyde, a shorter reaction time, and a lower temperature. The monoalkylated derivatives are the N-alkyl derivatives where a hydrogen atom of one amino group is replaced by an alkyl or a substituted alkyl group. Generally, the amino group of the (4-epi-vancosaminyl)-O-glucosyl group, when present, is alkylated first, to prepare formula I compounds where $R_2$ is alkyl or substituted alkyl and $R_1$ and $R_3$ are hydrogen. A large excess of the aldehyde favors the formation of dialkylated and trialkylated derivatives of the formula II compounds and the formation of dialkylated derivatives of the formula III and IV compounds. The dialkylated derivatives are the N-alkyl derivatives where a hydrogen atom of two of the amino groups is replaced by an alkyl or substituted alkyl group. Generally, this group of derivatives of the formula II compounds includes the formula I compounds where $R_2$ and either $R_1$ or $R_3$ is an alkyl or substituted alkyl group and R is a (4-epi-vancosaminyl)-O-glucosyl group. The dialkylated derivatives of the formula III and IV compounds are the formula I compounds where $R_1$ and $R_3$ are alkyl or substituted alkyl groups and R is the glucosyl group and hydrogen, respectively. The trialkylated derivatives are the formula I compounds where R is a (4-epi-vancosaminyl)-O-glucosyl group and $R_1$, $R_2$, and $R_3$ are alkyl or substituted alkyl groups.

The N-alkyl derivatives of this invention include the formula I compounds where $R_1$, $R_2$ and $R_3$ are independently $C_1$ to $C_{12}$ alkyl or hydrogen. The preferred N-alkyl derivatives of this group are those where R is a (4-epi-vancosaminyl)-O-glucosyl group, $R_1$ and $R_3$ are hydrogen, and $R_2$ is $C_8$–$C_{12}$ alkyl. Examples of the preferred alkyl derivatives are those where $R_2$ is n-octyl, 2-methyloctyl, 3-methyloctyl, n-nonyl, 2-methylnonyl, n-decyl, 2-methyldecyl, n-undecyl, 2-methylundecyl, or n-dodecyl. More preferably, X and Y are chloro and $R_2$ is n-octyl, n-nonyl, or n-decyl.

The N-alkyl derivatives of this invention also include formula I compounds where $R_1$, $R_2$ and $R_3$ are independently hydrogen or a substituted alkyl group of formula:

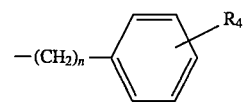

When n is 1, examples of this substituted alkyl group include: benzyl, p-fluorobenzyl, p-chlorobenzyl, p-bromobenzyl, p-iodobenzyl, m-fluorobenzyl, m-chlorobenzyl, m-bromobenzyl, m-iodobenzyl, o-fluorobenzyl, o-chlorobenzyl, o-bromobenzyl, o-iodobenzyl, p-methylbenzyl, p-ethylbenzyl, p-propylbenzyl, p-isopropylbenzyl, p-butylbenzyl, p-pentylbenzyl, p-hexylbenzyl, p-heptylbenzyl, p-octylbenzyl, m-methylbenzyl, m-ethylbenzyl, m-propylbenzyl, m-isopropylbenzyl, m-butylbenzyl, m-pentylbenzyl, m-hexylbenzyl, m-heptylbenzyl, m-octylbenzyl, o-methylbenzyl, o-ethylbenzyl, o-propylbenzyl, o-isopropylbenzyl, o-butylbenzyl, o-pentylbenzyl, o-hexylbenzyl, o-heptylbenzyl, o-octylbenzyl, p-methoxybenzyl, p-ethoxybenzyl, p-propoxybenzyl, p-isopropoxybenzyl, p-butoxybenzyl, p-pentoxybenzyl, p-hexyloxybenzyl, p-heptyloxybenzyl, p-octyloxybenzyl, m-methoxybenzyl, m-ethoxybenzyl, m-propoxybenzyl, m-isopropoxybenzyl, m-butoxybenzyl, m-pentoxybenzyl, m-hexyloxybenzyl, m-heptyloxybenzyl, m-octyloxybenzyl, o-methoxybenzyl, o-ethoxybenzyl, o-propoxybenzyl, o-isopropoxybenzyl, o-butoxybenzyl, o-pentoxybenzyl, o-hexyloxybenzyl, o-heptyloxybenzyl, o-octyloxybenzyl, p-aminobenzyl, p-methylaminobenzyl, p-dimethylaminobenzyl, p-ethylaminobenzyl, p-diethylaminobenzyl, p-propylaminobenzyl, p-dipropylaminobenzyl, m-aminobenzyl, m-methylaminobenzyl, m-dimethylaminobenzyl, m-ethylaminobenzyl, m-diethylaminobenzyl, m-propylaminobenzyl, m-dipropylaminobenzyl, o-aminobenzyl, o-methylaminobenzyl, o-dimethylaminobenzyl, o-ethylaminobenzyl, o-diethylaminobenzyl, o-propylaminobenzyl, or o-dipropylaminobenzyl.

Preferably, $R_4$ is halo, $C_6$–$C_8$ alkyl, $C_6$–$C_8$ alkoxy, or di($C_1$–$C_3$)alkylamino. The preferred examples of this group are p-bromobenzyl, p-chlorobenzyl, p-fluorobenzyl, m-chlorobenzyl, o-chlorobenzyl, p-octylbenzyl, p-octyloxybenzyl, and p-diethylaminobenzyl. More preferably, the substituted alkyl group is p-bromobenzyl, p-octylbenzyl, p-octyloxybenzyl, or p-diethylaminobenzyl.

Preferably, when $R_4$ is halo, $C_6$–$C_8$alkyl, $C_6$–$C_8$ alkoxy, or di($C_1$–$C_3$)alkylamino, X and Y are chloro. More preferably, R is a (4-epi-vancosaminyl)-O-glucosyl group and $R_1$ and $R_3$ are hydrogen. Most preferably, $R_2$ is p-bromobenzyl, p-octylbenzyl, p-octyloxybenzyl, or diethylaminobenzyl.

When n is 2, examples of this substituted alkyl group include: phenylethyl, (p-fluorophenyl)ethyl, (p-chlorophenyl)ethyl, (p-bromophenyl)ethyl, (p-methylphenyl)ethyl, (p-ethylphenyl)ethyl, (p-methoxyphenyl)ethyl, and (p-dimethylaminophenyl)ethyl. Preferably, the substituted alkyl group is phenylethyl ($R_4$ is hydrogen). More preferably, R is a (4-epi-vancosaminyl)-O-glucosyl group, $R_2$ is phenylethyl, X and Y are chloro, and $R_1$ and $R_3$ are hydrogen.

When n is 3, examples of this substituted alkyl group include: phenylpropyl, (p-fluorophenyl)propyl, (p-chlorophenyl)propyl, (p-bromophenyl)propyl, (p-methylphenyl)propyl, (p-ethylphenyl)propyl, (p-methoxyphenyl)ropyl, and (p-dimethylaminophenyl)propyl. Preferably, the substituted alkyl group is phenylpropyl ($R_4$ is hydrogen).

The N-alkyl derivatives of this invention also include compounds of formula I where the alkyl group is a substituted alkyl group of formula:

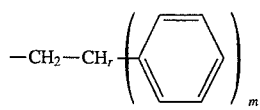

Examples of this group are diphenylethyl (m=2, r=1) and triphenylethyl (m=3, r=0). Preferably, X and Y are chloro, R is a (4-epi-vancosaminyl)-O-glucosyl group, $R_3$ is hydrogen, and $R_1$ and $R_2$ are either hydrogen or diphenylethyl.

The N-acyl derivatives of this invention are prepared by the reaction of a formula II, III, or IV compound with an activated ester of the alkanoic acid of the desired acyl group. The term "activated ester" means an ester which renders the carboxyl function of the acylating group reactive to coupling with the amino group of the glycopeptide. The preferred activated ester is the 2,4,5-trichlorophenyl ester. The reaction is carried out in a polar organic solvent, such as dimethylformamide, at a temperature of about 50° C. to about 110° C. for 1 to 5 hours. The reaction for the formation of the N-acyl derivatives is preferably carried out at a temperature of about 70° C. to about 80° C. for about 2 to 4 hours.

The ratio of the activated ester to the formula II, III, or IV compound and the reaction conditions determines the products of the reaction. The formation of monoacylated derivatives is favored by using a slight excess of the activated ester and a short reaction time. The monoacylated derivatives are the N-acyl derivatives where a hydrogen atom of one of the amino groups is replaced by an alkanoyl or substituted alkanoyl group. Generally, the monoacylated derivatives of the formula II compounds are the formula I compounds where R is a (4-epi-vancosaminyl)-O-glucosyl group and either $R_1$, $R_2$, or $R_3$ is an alkanoyl or substituted alkanoyl group. The monoacylated derivatives of the formula III or IV compounds are the formula I compounds where either $R_1$ or $R_3$ is an alkanoyl or substituted alkanoyl group and R is the glucosyl group or hydrogen, respectively. The diacylated and triacylated derivatives of the formula II compounds and the diacylated derivatives of the formula III and IV compounds are produced using a large excess of the active ester. The diacylated derivatives are the N-acyl derivatives where a hydrogen atom of two of the amino groups is replaced by an alkanoyl or substituted alkanoyl group. Generally, this group of derivatives of the formula II compounds includes the formula I compounds where R is a (4-epi-vancosaminyl)-O-glucosyl group, two of $R_1$, $R_2$, and $R_3$ are alkanoyl or substituted alkanoyl groups. The diacylated derivatives of the formula III or IV compounds are the formula I compounds where $R_1$ and $R_3$ are both alkanoyl or substituted alkanoyl groups, and R is the glucosyl group or hydrogen, respectively. The triacylated derivatives are the derivatives of the formula II compounds where $R_1$, $R_2$, and $R_3$ are alkanoyl or substituted alkanoyl groups.

The N-acyl derivatives of this invention include the formula I compounds where $R_1$, $R_2$, and $R_3$ are independently $C_2$ to $C_9$ alkanoyl or hydrogen. Examples of the acyl derivatives, e.g., are acetyl, propionyl, isopropionyl, n-butyryl, n-pentanoyl, n-hexanoyl, n-heptanoyl, n-octanoyl, and n-nonanoyl. The preferred acyl groups are n-butyryl, n-pentanoyl, n-hexanoyl, and n-heptanoyl. Preferably, R is a (4-epi-vancosaminyl)-O-glucosyl group, $R_3$ is hydrogen and either $R_1$ or $R_2$ is an acyl group.

The N-acyl derivatives of this invention also include formula I compounds where $R_1$, $R_2$, and $R_3$ are independently hydrogen or a substituted alkanoyl group of formula:

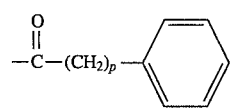

Examples of this substituted acyl group are benzoyl, phenylacetyl, and phenylpropionyl. Preferably, R is a (4-epi-vancosaminyl)-O-glucosyl group, $R_3$ is hydrogen and either $R_1$ or $R_2$ is a substituted acyl group.

Examples of compounds that have been prepared and are a part of this invention are listed in Tables I, II, and III for the formula I compounds.

TABLE I

Examples of Formula I Compounds
X = H, Y = Cl,
R = (4-epi-vancosaminyl)-O-glucosyl group

| Compound No. | $R_1$ | $R_2$ | $R_3$ |
|---|---|---|---|
| 1 | H | n-octyl | H |
| 2 | H | H | n-octyl |
| 3 | H | n-octyl | n-octyl |
| 4 | n-octyl | n-octyl | n-octyl |
| 5 | H | n-pentyl | H |
| 6 | H | H | n-pentyl |
| 7 | H | n-pentyl | n-pentyl |
| 8 | n-pentyl | n-pentyl | n-pentyl |
| 9 | H | n-decyl | H |
| 10 | H | benzyl | H |
| 11 | benzyl | benzyl | H |
| 12 | benzyl | benzyl | benzyl |
| 13 | H | 4-pentylbenzyl | 4-pentylbenzyl |
| 14 | 4-pentylbenzyl | 4-pentylbenzyl | 4-pentylbenzyl |
| 15 | H | 4-octylbenzyl | H |
| 16 | H | 4-octyloxybenzyl | H |
| 17 | H | 4-diethylaminobenzyl | H |
| 18 | H | p-bromobenzyl | H |
| 19 | p-bromobenzyl | p-bromobenzyl | H |
| 20 | H | p-chlorobenzyl | H |
| 21 | p-chlorobenzyl | H | H |
| 22 | H | H | p-chlorobenzyl |
| 23 | p-chlorobenzyl | p-chlorobenzyl | H |
| 24 | H | phenylethyl | H |
| 25 | phenylethyl | H | H |
| 26 | H | diphenylethyl | H |
| 27 | H | n-heptanoyl | H |
| 28 | H | phenylpropionyl | H |
| 29 | phenylpropionyl | H | H |
| 30 | H | n-butyryl | H |
| 31 | H | H | n-butyryl |
| 32 | n-butyryl | H | H |
| 33 | n-butyryl | n-butyryl | H |

TABLE II

Examples of Formula I Compounds
X, Y = Cl
R = (4-epi-vancosaminyl)-O-glucosyl group

| Compound No. | $R_1$ | $R_2$ | $R_3$ |
|---|---|---|---|
| 34 | H | n-pentyl | H |
| 35 | H | H | n-pentyl |
| 36 | H | n-pentyl | n-pentyl |
| 37 | n-pentyl | n-pentyl | n-pentyl |
| 38 | H | n-octyl | H |
| 39 | H | H | n-octyl |
| 40 | n-octyl | H | n-octyl |
| 41 | n-octyl | n-octyl | H |
| 42 | H | n-decyl | H |
| 43 | H | phenylethyl | H |
| 44 | phenylethyl | H | H |
| 45 | H | diphenylethyl | H |
| 46 | diphenylethyl | H | H |
| 48 | H | phenylpropyl | H |
| 49 | H | H | phenylpropyl |
| 50 | phenylpropyl | phenylpropyl | H |
| 51 | H | benzyl | H |
| 52 | H | H | benzyl |
| 53 | benzyl | benzyl | H |
| 54 | H | 4-octylbenzyl | H |
| 55 | H | 4-octyloxybenzyl | H |
| 56 | H | p-diethylaminobenzyl | H |
| 57 | p-diethylaminobenzyl | p-diethylaminobenzyl | H |
| 58 | H | p-bromobenzyl | H |
| 59 | p-bromobenzyl | p-bromobenzyl | H |
| 60 | H | p-chlorobenzyl | H |
| 61 | p-chlorobenzyl | p-chlorobenzyl | H |
| 62 | H | o-chlorobenzyl | H |
| 64 | H | m-chlorobenzyl | H |
| 65 | m-chlorobenzyl | m-chlorobenzyl | H |
| 66 | p-fluorobenzyl | H | H |
| 67 | H | p-fluorobenzyl | H |
| 68 | p-fluorobenzyl | p-fluorobenzyl | H |
| 69 | n-heptanoyl | H | H |

TABLE III

Examples of Formula I Compounds
(Y = Cl)

| Compound No. | $R_1$ | $R_3$ | R | X |
|---|---|---|---|---|
| 70 | benzyl | H | glucosyl | H |
| 71 | n-pentyl | H | glucosyl | H |
| 72 | n-pentyl | n-pentyl | glucosyl | H |
| 73 | benzyl | H | H | H |
| 74 | n-pentyl | H | H | H |
| 75 | n-pentyl | n-pentyl | H | H |
| 76 | benzyl | H | glucosyl | Cl |
| 77 | n-pentyl | H | glucosyl | Cl |
| 78 | n-pentyl | n-pentyl | glucosyl | Cl |
| 79 | benzyl | H | H | Cl |

The formula I compounds have in vitro and in vivo activity against Gram-positive pathogenic bacteria. The minimal inhibitory concentrations (MIC's) at which the formula I compounds inhibit certain bacteria are given in Table IV. The MIC's were determined using a standard agar-dilution assays.

TABLE IV

In Vitro Activity of Formula I Compounds
MIC (mcg/ml)

| Organism | 1 | 6 | 7 | 10 | 11 | 12 |
|---|---|---|---|---|---|---|
| *Staphylococcus aureus* NRRL X1.1 | 1 | .25 | 1 | .25 | .25 | 8 |
| *Staphylococcus aureus* V41 | 1 | .25 | 1 | .25 | .5 | 8 |
| *Staphylococcus aureus* X400 | 1 | .25 | 1 | .5 | .5 | 8 |
| *Staphylococcus aureus* S13E | .5 | .25 | 1 | .125 | .25 | 4 |
| *Staphylococcus epidermidis* EPI270 | 1 | .5 | 2 | .25 | 1 | 8 |
| *Staphylococcus epidermidis* 222 | 1 | .5 | 1 | .25 | .5 | 8 |
| *Streptococcus pyogenes* C203 | .25 | .125 | .5 | .25 | .25 | 2 |
| *Streptococcus pneumoniae* Park 1 | .5 | .125 | .5 | .125 | .25 | 2 |
| *Enterococcus faecium* X66[b] | 1 | 1 | 2 | .25 | .25 | 4 |
| *Enterococcus faecalis* 2041[c] | 1 | 1 | 2 | .5 | 1 | 8 |
| *Haemophilus influenzae* C.L. | >128 | >128 | >128 | >128 | >128 | >128 |
| *Haemophilus influenzae* 76 | >128 | >128 | >128 | >128 | >128 | >128 |
| *Escherichia coli* N10 | >128 | >128 | >128 | >128 | >128 | >128 |
| *Escherichia coli* EC14 | >128 | >128 | >128 | >128 | >128 | >128 |
| *Escherichia coli* TEM | >128 | >128 | >128 | >128 | >128 | >128 |
| *Klebsiella pneumoniae* X26 | >128 | >128 | >128 | >128 | >128 | >128 |
| *Klebsiella pneumoniae* X68 | >128 | >128 | >128 | >128 | >128 | >128 |
| *Klebsiella pneumoniae* KAE | >128 | >128 | >128 | >128 | >128 | >128 |

| Organism | 13 | 17 | 18 | 21 | 23 | 24 |
|---|---|---|---|---|---|---|
| *Staphylococcus aureus* NRRL X1.1 | 4 | .5 | 1 | .5 | 2 | .5 |
| *Staphylococcus aureus* V41 | 4 | .5 | 1 | .5 | 2 | .5 |
| *Staphylococcus aureus* X400 | 4 | .5 | 1 | .5 | 2 | 1 |
| *Staphylococcus aureus* S13E | 4 | .5 | 1 | .25 | 2 | 1 |
| *Staphylococcus epidermidis* EPI270 | 4 | 1 | 1 | .5 | 2 | .5 |
| *Staphylococcus epidermidis* 222 | 4 | .5 | .5 | .25 | 1 | .5 |

TABLE IV-continued

In Vitro Activity of Formula I Compounds
MIC (mcg/ml)

| | Compound Number[a] | | | | | |
|---|---|---|---|---|---|---|
| Streptococcus pyogenes C203 | 2 | .25 | .125 | .5 | 2 | .25 |
| Streptococcus pneumoniae Park 1 | 1 | .25 | .25 | .5 | 1 | .25 |
| Enterococcus faecium X66[b] | 2 | 1 | 1 | .5 | 4 | .5 |
| Enterococcus faecalis 2041[c] | 4 | 1 | 1 | .5 | 4 | .5 |
| Haemophilus influenzae C.L. | >128 | >128 | >128 | >128 | >128 | >128 |
| Haemophilus influenzae 76 | >128 | >128 | >128 | >128 | >128 | >128 |
| Escherichia coli N10 | >128 | >128 | >128 | >128 | >128 | >128 |
| Escherichia coli EC14 | >128 | >128 | >128 | >128 | >128 | >128 |
| Escherichia coli TEM | >128 | >128 | >128 | >128 | >128 | >128 |
| Klebsiella pneumoniae X26 | >128 | >128 | >128 | >128 | >128 | >128 |
| Klebsiella pneumoniae X68 | >128 | >128 | >128 | >128 | >128 | >128 |
| Klebsiella pneumoniae KAE | >128 | >128 | >128 | >128 | >128 | >128 |

| Organism | 27 | 34 | 35 | 38 | 42 | 43 |
|---|---|---|---|---|---|---|
| Staphylococcus aureus NRRL X1.1 | 1 | .5 | .5 | .5 | .5 | .25 |
| Staphylococcus aureus V41 | 1 | .5 | .25 | 1 | .5 | .5 |
| Staphylococcus aureus X400 | 1 | 1 | .5 | 1 | .5 | 1 |
| Staphylococcus aureus S13E | 2 | .5 | .25 | .5 | 1 | 1 |
| Staphylococcus epidermidis EPI270 | 2 | 2 | 1 | 1 | 1 | 1 |
| Staphylococcus epidermidis 222 | 2 | .5 | .5 | .5 | .5 | .25 |
| Streptococcus pyogenes C203 | .5 | .5 | .25 | .06 | .25 | .5 |
| Streptococcus pneumoniae Park 1 | .25 | .5 | .25 | .25 | .25 | .125 |
| Enterococcus faecium X66[b] | 2 | .5 | .5 | .25 | .06 | 1 |
| Enterococcus faecalis 2041[c] | 2 | 1 | .5 | .25 | .5 | .5 |
| Haemophilus influenzae C.L. | >128 | >128 | >128 | >128 | >128 | >128 |
| Haemophilus influenzae 76 | >128 | >128 | >128 | >128 | >128 | >128 |
| Escherichia coli N10 | >128 | >128 | >128 | >128 | >128 | >128 |
| Escherichia coli EC14 | >128 | >128 | >128 | >128 | >128 | >128 |
| Escherichia coli TEM | >128 | >128 | >128 | >128 | >128 | >128 |
| Klebsiella pneumoniae X26 | >128 | >128 | >128 | >128 | >128 | >128 |
| Klebsiella pneumoniae X68 | >128 | >128 | >128 | >128 | >128 | >128 |
| Klebsiella pneumoniae KAE | >128 | >128 | >128 | >128 | >128 | >128 |

| Organism | 45 | 51 | 54 | 55 | 56 | 58 |
|---|---|---|---|---|---|---|
| Staphylococcus aureus NRRL X1.1 | .25 | .25 | 32 | 8 | .5 | .5 |
| Staphylococcus aureus V41 | .5 | .5 | 64 | 4 | .5 | .5 |
| Staphylococcus aureus X400 | .5 | .5 | 64 | 16 | 1 | 1 |
| Staphylococcus aureus S13E | .5 | .25 | 64 | 8 | 1 | 1 |
| Staphylococcus epidermidis EPI270 | 1 | 1 | 64 | 16 | 2 | 2 |
| Staphylococcus epidermidis 222 | .5 | .5 | 64 | 8 | .5 | .5 |
| Streptococcus pyogenes C203 | .125 | .25 | 8 | 4 | .5 | .125 |
| Streptococcus pneumoniae Park 1 | .25 | .125 | 4 | 2 | .5 | .125 |
| Enterococcus faecium X66[b] | .5 | .25 | 64 | 8 | 1 | .25 |
| Enterococcus faecalis 2041[c] | .5 | .5 | 64 | 8 | .5 | .25 |
| Haemophilus influenzae C.L. | >128 | >128 | >128 | >128 | >128 | >128 |
| Haemophilus influenzae 76 | >128 | >128 | >128 | >128 | >128 | >128 |
| Escherichia coli N10 | >128 | >128 | >128 | >128 | >128 | >128 |
| Escherichia coli EC14 | >128 | >128 | >128 | >128 | >128 | >128 |
| Escherichia coli TEM | >128 | >128 | >128 | >128 | >128 | >128 |
| Klebsiella pneumoniae X26 | >128 | >128 | >128 | >128 | >128 | >128 |
| Klebsiella pneumoniae X68 | >128 | >128 | >128 | >128 | >128 | >128 |
| Klebsiella pneumoniae KAE | >128 | >128 | >128 | >128 | >128 | >128 |

| Organism | 60 | 62 | 64 | 66 | 67 | 69 |
|---|---|---|---|---|---|---|
| Staphylococcus aureus NRRL X1.1 | .125 | .5 | .25 | .5 | .5 | 1 |
| Staphylococcus aureus V41 | .25 | .5 | .25 | 1 | 1 | 2 |
| Staphylococcus aureus X400 | .5 | 1 | .5 | 1 | 1 | 4 |
| Staphylococcus aureus S13E | NT | 1 | .5 | 1 | 1 | 2 |
| Staphylococcus epidermidis EPI270 | .5 | 1 | .25 | 2 | 2 | 8 |
| Staphylococcus epidermidis 222 | .25 | .5 | .5 | 1 | .5 | 2 |
| Streptococcus pyogenes C203 | .06 | .125 | .06 | .5 | .25 | 1 |
| Streptococcus pneumoniae Park 1 | .06 | .125 | .25 | .25 | .125 | .5 |
| Enterococcus faecium X66[b] | .25 | .25 | .25 | 1 | .5 | 2 |
| Enterococcus faecalis 2041[c] | .25 | .5 | .25 | 1 | .5 | 1 |
| Haemophilus influenzae C.L. | >128 | >128 | >128 | >128 | >128 | >128 |
| Haemophilus influenzae 76 | >128 | >128 | >128 | >128 | >128 | >128 |
| Escherichia coli N10 | >128 | >128 | >128 | >128 | >128 | >128 |
| Escherichia coli EC14 | >128 | >128 | >128 | >128 | >128 | >128 |
| Escherichia coli TEM | >128 | >128 | >128 | NG | NG | >128 |
| Klebsiella pneumoniae X26 | >128 | >128 | >128 | >128 | >128 | >128 |
| Klebsiella pneumoniae X68 | >128 | >128 | >128 | >128 | >128 | >128 |

TABLE IV-continued

In Vitro Activity of Formula I Compounds
MIC (mcg/ml)

| | Compound Number[a] | | | | | |
|---|---|---|---|---|---|---|
| Klebsiella pneumoniae KAE | >128 | >128 | >128 | >128 | >128 | >128 |

| Organism | 70 | 71 | 73 | 74 | 76 | 77 | 79 |
|---|---|---|---|---|---|---|---|
| Staphylococcus aureus NRRL X1.1 | 2 | 2 | 1 | 4 | .25 | .5 | .25 |
| Staphylococcus aureus V41 | 2 | 2 | 1 | 4 | .25 | .5 | .25 |
| Staphylococcus aureus X400 | 2 | 4 | 1 | 4 | .25 | 1 | .5 |
| Staphylococcus aureus S13E | 2 | 2 | 1 | 4 | .25 | .5 | .25 |
| Staphylococcus epidermidis EPI270 | .5 | 1 | .25 | 2 | 2 | 8 | |
| Staphylococcus epidermidis 222 | 2 | 4 | 2 | 4 | .5 | 1 | .5 |
| Streptococcus pyogenes C203 | 2 | 2 | 1 | 4 | .5 | .25 | .25 |
| Streptococcus pneumoniae Park 1 | 2 | 2 | 1 | 4 | 1 | .5 | .25 |
| Enterococcus faecium X66[b] | 2 | 8 | 1 | 8 | 1 | 2 | 1 |
| Enterococcus faecalis 2041[c] | 2 | 8 | 2 | 8 | 1 | 2 | 1 |
| Haemophilus influenzae C.L. | >128 | >128 | >128 | >128 | >128 | 128 | >128 |
| Haemophilus influenzae 76 | >128 | >128 | >64 | >128 | >128 | 128 | >128 |
| Escherichia coli N10 | >128 | >128 | >128 | >128 | >128 | >128 | >128 |
| Escherichia coli EC14 | >128 | >128 | >128 | >128 | >128 | >128 | >128 |
| Escherichia coli TEM | >128 | >128 | >128 | >128 | >128 | >128 | >128 |
| Klebsiella pneumoniae X26 | >128 | >128 | >128 | >128 | >128 | >128 | >128 |
| Klebsiella pneumoniae X68 | >128 | >128 | >128 | >128 | >128 | >128 | >128 |
| Klebsiella pneumoniae KAE | >128 | >128 | >128 | >128 | >128 | >128 | >128 |

[a]Compound Numbers from Tables I, II and III
[b]Formerly Streptococcus faecium X66
[c]Formerly Streptococcus faecalis 2041

The formula I compounds have also shown in vivo antimicrobial activity against experimentally-induced infections in laboratory animals. When two doses of test compound were administered to mice experimentally infected with the test organism, the activity observed was measured as an $ED_{50}$ value [effective dose in mg/kg to protect 50% of the test animals: see W. Wick et al., J. Bacteriol., 81, 233–235 (1961)]. $ED_{50}$ values observed for illustrative compounds are given in Table V.

TABLE V

In Vivo Activity of Formula I Compounds
$ED_{50}$ (mg/kg/2)[a]

| Organism | Compound Numbers[b] | | | | | |
|---|---|---|---|---|---|---|
| | 1 | 2 | 5 | 6 | 7 | 8 |
| Staphylococcus aureus | 3.35 | >5.0 | 0.92 | 0.88 | 4.09 | >4.0 |
| Streptococcus pyogenes | 0.43 | 0.79 | 0.17 | 0.67 | 0.83 | 2.69 |
| Streptococcus pneumoniae | 0.43 | 1.25 | 0.1 | 0.94 | 0.98 | >4.0 |

| Organism | 9 | 10 | 11 | 13 | 17 | 18 |
|---|---|---|---|---|---|---|
| Staphylococcus aureus | | 0.46 | 0.58 | | 0.78 | 1.74 |
| Streptococcus pyogenes | 0.68 | 0.2 | 0.34 | 0.37 | 0.23 | 0.15 |
| Streptococcus pneumoniae | | 0.4 | 0.37 | 1.26 | 0.33 | 0.25 |

| Organism | 20 | 21 | 23 | 24 | 25 | 26 |
|---|---|---|---|---|---|---|
| Staphylococcus aureus | >2.0 | | | 0.72 | >1.0 | >3.0 |
| Streptococcus pyogenes | 0.15 | 0.29 | 0.8 | 0.09 | 0.50 | 0.48 |

TABLE V-continued

In Vivo Activity of Formula I Compounds
$ED_{50}$ (mg/kg/2)[a]

| | Compound Numbers[b] | | | | | |
|---|---|---|---|---|---|---|
| Streptococcus pneumoniae | 0.23 | 0.47 | 1.02 | 0.25 | 0.76 | 0.47 |

| Organism | 27 | 34 | 36 | 37 | 38 | 39 |
|---|---|---|---|---|---|---|
| Staphylococcus aureus | >1.0 | 0.77 | 1.0 | >5.0 | 0.43 | 1.22 |
| Streptococcus pyogenes | 0.5 | 0.44 | 0.38 | 1.09 | 0.11 | 0.18 |
| Streptococcus pneumoniae | 0.71 | 0.44 | 0.29 | 0.88 | 0.062 | 0.34 |

| Organism | 41 | 42 | 43 | 44 | 45 | 46 |
|---|---|---|---|---|---|---|
| Staphylococcus aureus | 1.22 | 0.67 | 0.125 | 0.3 | 0.77 | 0.75 |
| Streptococcus pyogenes | 0.18 | 0.09 | 0.38 | 0.125 | 0.1 | 0.14 |
| Streptococcus pneumoniae | 0.32 | 0.09 | 0.11 | 0.2 | 0.1 | 0.22 |

| Organism | 50 | 51 | 52 | 53 | 54 | 55 |
|---|---|---|---|---|---|---|
| Staphylococcus aureus | >5.0 | 0.34 | | 1.25 | | |
| Streptococcus pyogenes | 0.6 | 0.16 | 0.5 | 0.2 | 0.91 | 0.73 |
| Streptococcus pneumoniae | 1.02 | 0.35 | 0.75 | 0.18 | | |

| Organism | 56 | 57 | 58 | 59 | 60 | 61 |
|---|---|---|---|---|---|---|
| Staphylococcus aureus | 0.65 | | 0.38 | 3.16 | 0.25 | 1.83 |

TABLE V-continued

In Vivo Activity of Formula I Compounds
ED$_{50}$ (mg/kg/2)[a]

Compound Numbers[b]

| | | | | | | |
|---|---|---|---|---|---|---|
| Streptococcus pyogenes | .06 | <0.62 | 0.05 | 0.25 | 0.06 | 0.10 |
| Streptococcus pneumoniae | .09 | | 0.08 | <0.31 | 0.08 | 0.08 |

| Organism | 62 | 63 | 64 | 65 | 66 | 67 |
|---|---|---|---|---|---|---|
| Staphylococcus aureus | 0.77 | 1.49 | 0.55 | 1.59 | 0.37 | 0.33 |
| Streptococcus pyogenes | 0.20 | 0.50 | 0.94 | 0.15 | 0.18 | <0.12 |
| Streptococcus pneumoniae | 0.17 | 0.18 | 0.10 | 0.11 | 0.22 | <0.12 |

| Organism | 68 | 69 | 70 | 73 | 76 | 79 |
|---|---|---|---|---|---|---|
| Staphylococcus aureus | 0.80 | | 4.10 | >8.0 | 0.87 | >1.0 |
| Streptococcus pyogenes | 0.09 | <0.62 | 2.38 | 7.30 | 0.62 | 0.71 |
| Streptococcus pneumoniae | 0.12 | | 3.76 | >8.0 | 0.42 | 0.71 |

[a]doses administered subcutaneously to mice 1 and 4 hours post-infection
[b]Compound Numbers from Tables I, II and III One important aspect of the antimicrobial activity of the formula I compounds is their activity against vancomycin-resistant enterococci. This activity is illustrated in Table VI, which summarizes a comparison of the activity of illustrative compounds against representative vancomycin-resistant and vancomycin-susceptible enterococci, as determined using the standard agar-dilution assay. End points were read after 24-hour incubation. The ratio was calculated by dividing the mean MIC of the compound against the vancomycin-resistant strains by the mean MIC of the compound against the vancomycin-susceptible strains. A high ratio indicates that the compound is much less active against the vancomycin-resistant strains when compared to the vancomycin-susceptible strains. The formula I compounds are generally active against the vancomycin-resistant strains as evidenced by mean minimum inhibitory concentration in the range of about 2 to about 10 mcg/mL.

TABLE VI

Suceptibility of vancomycin-resistant (Vanco$^r$)
and vancomycin-susceptible (Vanco$^s$)
E. faecium and E. faecalis
Geometric Mean MIC (mcg/mL)

| Compound No. | Vanco$^r$ Strains (n = 25) | Vanco$^s$ Strains (n = 34) | Ratio |
|---|---|---|---|
| 1 | 9.7 | 2.2 | 4.9 |
| 38 | 2.1 | 0.73 | 2.9 |
| 42 | 2.5 | 0.92 | 2.7 |
| 43 | 4.0 | 0.77 | 5.2 |
| 45 | 9.4 | 1.7 | 5.5 |
| 56 | 5.1 | 0.73 | 7.0 |
| 58 | 3.1 | 0.67 | 4.6 |
| 60 | 3.6 | 0.65 | 5.5 |
| A82846B | 9.4 | 0.51 | 18.4 |

Another important property of the formula I compounds is the low binding of the compounds to serum proteins when compared with other glycopeptide antibiotics. The minimal inhibitory concentrations (MIC's) were measured for selected compounds against six vancomycin-susceptible strains of staphylococci and enterococci. The MIC's were measured both in the absence (−) and presence (+) of human serum, broth supplemented with human serum to 40%. The MIC's were determined in a serial dilution assay using 0.2 mL volumes of medium with ~10$^5$ bacteria per milliliter. The results are shown in Table VII. The ratio of the MIC measured in the presence of added serum to the MIC measured in the absence of added serum ("ratio") is an indication of the degree of serum binding. A ratio of about one indicates that the presence of serum has no effect on the in vitro antimicrobial activity and the compound is not highly serum bound. A ratio that is greater than one, for example about ten, indicates the compound has a high degree of serum binding.

TABLE VII

Effect of Human Serum on the MIC

| Compound No. | −[a] | +[b] | ratio |
|---|---|---|---|
| 38 | 0.75 | 0.43 | 0.58 |
| 42 | 0.87 | 0.66 | 0.76 |
| 58 | 0.43 | 1.0 | 2.3 |
| 60 | 0.76 | 1.5 | 2.0 |
| A82846B | 0.5 | 0.75 | 1.5 |
| Teicoplanin | 0.25 | 3.8 | 12.6 |

[a]MIC determined in absence of added serum
[b]MIC determined in presence of human serum The formula I compounds exhibited an unexpectedly low level of serum binding. A ratio of about two, see Table VII, indicates the compound is approximately 50% serum bound. This level of binding is similar to the level exhibited by vancomycin. Previously, N-alkyl derivatives of vancomycin were found to exhibit a higher degree of serum binding, ratio in the range of five to ten, than that exhibited by vancomycin. The alkylation of one or more amino groups of vancomycin was considered the cause of the increase in serum protein binding. However, the formula I compounds unexpectedly exhibit approximately the same level of serum binding as the parent compound, i.e., A82846B.

Pharmaceutical formulations of the formula I compounds are also part of this invention. Thus, the compound, preferably in the form of a pharmaceutically acceptable salt, can be formulated for oral or parenteral administration for the therapeutic or prophylactic treatment of bacterial infections.

For example, the compound can be admixed with conventional pharmaceutical carriers and excipients and used in the form of tablets, capsules, elixirs, suspensions, syrups, wafers and the like. The compositions comprising a formula I compound will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more attractive in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic, preferably in its salt form, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The compounds of this invention are particularly useful in treating infections caused by methicillin-resistant staphylococci. Also, the compounds are useful in treating infection due to enterococci. Examples of such diseases are severe staphylococcal infections, i.e., staphylococcal endocarditis and staphylococcal septicemia. The animal may be either susceptible to, or infected with, the microorganism. The method comprises administering to the animal an amount of a formula I compound which is effective for this purpose. In general, an effective amount of a formula I compound is a dose between about 0.5 and about 100 mg/kg. A preferred dose is from about 1 to about 60 mg/kg of active compound. A typical daily dose for an adult human is from about 50 mg to about 1.0 g.

In practicing this method, the antibiotic can be administered in a single daily dose or in multiple doses per day. The treatment regime may require administration over extended periods of time, e.g., for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via intraveneous infusion. In this procedure a sterile formulation of a suitable soluble salt of the antibiotic is incorporated in a physiological fluid, such as 5% dextrose solution, and the resulting solution is infused slowly IV. Alternatively, the piggy-back method of IV infusion can also be used.

In order to illustrate more fully the operation of this invention, the following examples are provided. Generally, the formula III or IV compounds are prepared as described in Preparations 1 and 2. The N-alkyl derivatives are prepared as described in Examples 1 and 2. Also, the N-acyl derivatives are prepared as described in Examples 3 and 4.

PREPARATION 1

Preparation of Compounds IIIa and IVa

A82846A (500 mg, 0.32 mmol) was dissolved in trifluoroacetic acid (100 mL) containing anisole (10 mL). The reaction mixture was stirred for 24 hours at room temperature under nitrogen. Volatile solvents were removed under vacuum to give a gray-tan residue. The residue was triturated with diethyl ether/chloroform (1:1, 50 mL×2). The solid material thus obtained (trifluoroacetic acid salt) was dissolved in water (~50 mL), and the pH of this solution was adjusted to 6.2 with pyridine. The solution was filtered, and the filtrate was lyophilized to give 426 mg of an off-white powder. High performance liquid chromatography (HPLC) analysis showed two major peaks (in the amounts of ~23% and 43%).

The two major products were separated by preparative-scale reverse-phase HPLC, using a WATERS PREPPAK-500/$C_{18}$ column (Milford, Mass., 57 mm×300 mm, 55–105∥ particles) eluting with an 8-L gradient of 1% aqueous pyridinium acetate to acetonitrile/1% aqueous pyridinium acetate (1:3) followed by 2 L of the latter. Fractions of 250 mL each were collected at a flow rate of 250 mL/min and were analyzed by thin layer chromatography (TLC) and HPLC.

Fractions containing IIIa (#10–16) were combined and lyophilized to give 82 mg of compound IIIa as a cream-colored solid. FAB Mass Spectrum (FAB-MS) (M+1): 1414 (accurate mass calcd. for $C_{66}H_{77}N_9O_{24}Cl=1414.4770$; found: 1414.40).

Fractions containing compound IVa (#27–29) were also combined and lyophilized to give 128 mg of compound IVa as a cream-colored powder. FAB-MS(M+1): 1252, 1109 (calculated for $C_{60}H_{67}N_9O_{19}Cl=1252.4242$; found: 1252.4240).

PREPARATION 2

Preparation of Compounds IIIb and IVb

A82846B (1 g) was dissolved in trifluoroacetic acid (200 mL) containing anisole (10 mL). The reaction mixture was stirred at room temperature for about two hours under nitrogen.

The reaction was worked up as described in Preparation 1 to give 1.12 g of the product mixture. FAB-MS(M+1): 1448, 1305, 1286, 1252, 1142. High performance liquid chromatographic analysis demonstrated that this material contained two major peaks (in amounts of ~42% and 43%, respectively).

Preparative reverse-phase HPLC, using the conditions described in Preparation 1, gave 283 mg of compound IIIb. FAB-MS(M+1): 1448 (calculated for $C_{66}H_{76}N_9O_{24}Cl_2=1448.4380$; found: 1448.4375).

The preparative reverse-phase hplc also yielded 270 mg of compound IVb. FAB-MS(P+1): 1286 (calculated for $C_{60}H66N_9O_{19}Cl_2=1286.3852$; found: 1286.3879).

EXAMPLE 1 (METHOD A)

Preparation of Compounds 1, 2, and 3

A82846A free base (293.5 mg, 0.19 mmol) was dissolved in a mixture of dimethylformamide and methanol (10 mL each). This solution was treated with n-octyl aldehyde (44.8 mg, 0.35 mmol) and stirred for 1¾ hours at 70° C. The solution was treated with sodium cyanoborohydride (75 mg, 1.19 mmol) and stirred for an additional 2 hours at 70° C. The reaction solution was concentrated in vacuo, the residue was diluted with water 25 mL, and this solution was lyophilized. The products were separated by reverse-phase high performance liquid chromatography (HPLC), using a WATERS μBONDAPAK $C_{18}$ column (19 mm×150 mm, 10μ particle, eluting with a 20 min. linear gradient of 15% acetonitrile/0.05% aqueous triethylamine phosphate (pH 3) to 60% acetonitrile/0.05% aqueous triethylamine phosphate (pH 3). The fractions containing the products, as shown by analytical HPLC, were desalted using HP-20SS resin (Mitsubishi Chemical Industries, Co., Ltd.) with methanol/0.1% acetic acid (8:2). The eluates were evaporated to dryness, treated with water, and lyophilized to give 36.6 mg of compound 1 (14.8% yield), 39.6 mg of compound 2 (16.0% yield), and 11.7 mg of compound 3 ( 3.5% yield).

EXAMPLE 2 (METHOD B)

Preparation of Compound 38

A82846B free base (1.1 g, 0.69 mmol) was dissolved in dimethylformamide (50 mL). This solution was treated with n-octyl aldehyde (195 mg, 1.52 mmol) and stirred for 30 minutes at 70° C. The solution was treated with sodium cyanoborohydride (162.6 mg, 2.5 mmol) and stirred for 90 minutes at 70° C. After allowing to cool to room temperature, the reaction solution was filtered. The residue was dissolved in 5% acetic acid in methanol (50 mL) and the solution was stirred at room temperature overnight. This solution was evaporated to dryness in vacuo, the residue treated with water 50 mL and n-butanol (a few drops), and lyophilized. The product was purified by reverse-phase HPLC, using a RAININ DYNAMAX $C_{18}$ column (50 mm×350 mm, 8μ particle, Woburn, Mass.) eluting with a 20 min. linear gradient of 20% acetonitrile/1% aqueous pyridinium acetate to 40% acetonitrile/1% aqueous pyridinium acetate to give 120 mg of compound 38 (10% yield).

EXAMPLE 3 (METHOD C)

Preparation of Compounds 28 and 29

A82846A free base (100.5 mg, 0.06 mmol) was dissolved in dimethylformamide 15 mL. This solution was treated with 3-phenylpropionic acid 2,4,5-trichlorophenyl ester (75 mg, 0.23 mmol) and stirred for 2 hours at 70° C. The solution was evaporated to dryness in vacuo; the residue was treated with water and lyophilized. The residue was triturated with dichloromethane 10 to remove the unreacted activated ester. The products were separated by reverse-phase HPLC, using a WATERS μBONDAPAK $C_{18}$ column (19 mm×150 mm), eluting with a 30 min. linear gradient of 15% acetonitrile/1% aqueous pyridinium acetate to 40% acetonitrile/1% aqueous pyridinium acetate to give 4.0 mg of compound 28 (3.7% yield) and 3.6 mg of compound 29 (3.3% yield).

EXAMPLE 4 (METHOD D)

Preparation of Compound 69

A82846B free base ( 195.4 mg, 0.12 mmol ) was dissolved in a mixture of dimethylformamide and methanol (10 mL of each). This solution was treated with n-heptanoic acid 2,4,5-trichlorophenyl ester 53 mg, 0.17 mmol and stirred for 4 hours at 110° C. The solution was evaporated to dryness in vacuo; the residue was treated with water and lyophilized. The residue was triturated with dichloromethane to remove the unreacted activated ester. The product was separated by reverse-phase HPLC, using a WATERS μBONDAPAK $C_{18}$ column (19 mm×150 mm) eluting with a 20 min. linear gradient of 15% acetonitrile/0.05% aqueous triethylamine phosphate (pH 3) to 35% acetonitrile/0.05% aqueous triethylamine phosphase (pH 3). The fractions containing the product were combined and desalted using HP-20SS resin, to give 7.6 mg of compound 69 (3.6% yield).

EXAMPLE 5

Tables VIII and IX summarize the preparation and certain physical characteristics of the exemplified compounds. The yield of the product was calculated using the amount of the formula II, III, or IV as the limiting reagent. The method of synthesis refers to the methods as described in Examples 1–4. The equivalents of reagent refers to the molar equivalents of either the aldehyde or the activated ester for the corresponding N-alkyl or N-acyl derivative relative to the amount of the formula II, III, or IV compound. The high performance liquid chromatography (HPLC) retention times ($t_R$) were measured using a WATERS μBONDAPAK $C_{18}$ column (3.9 mm×300 mm, 10μ particle), eluting with a 15 min. linear gradient of 5% acetonitrile/0.2% aqueous triethylamine phosphate buffer (pH=3) to 80% acetonitrile/ 0.2% aqueous triethylamine phosphate buffer (pH=3), using a flow rate of 1 mL/min. and ultraviolet detection at 280 nm.

TABLE VIII

Method of Synthesis and Physical Characteristics

| Compound No. | Yield (%) | Method | Reagent[a] (Equiv.) | Rxn. Time[b] (min.) | FAB-MS (M + H) | $t_R$ (min.) |
|---|---|---|---|---|---|---|
| 1 | 14.8 | A | 1.8 | 105 | 1669 | 11.35 |
| 2 | 16.0 | A | 1.8 | 105 | 1669 | 11.60 |
| 3 | 3.5 | A | 1.8 | 105 | 1781 | 13.75 |
| 4 | 8.2 | A | 10.0 | 60[c] | 1893 | 14.79 |
| 5 | 5.2 | A | 2.0 | 120[c] | 1627 | 8.43 |
| 6 | 6.6 | A | 2.0 | 120[c] | 1627 | 9.21 |
| 7 | 3.8 | A | 2.0 | 120[c] | 1697 | 10.44 |
| 8 | 2.2 | B | 3.5 | 55 | 1767 | 15.10 |
| 9 | 8.0 | B | 3.8 | 90 | 1697 | 12.17 |
| 10 | 11.4 | B | 3.5 | 30 | 1647 | 8.71 |
| 11 | 42.5 | B | 5.0 | 80 | 1737 | 8.61[d] |
| 12 | 11.9 | B | 5.0 | 80 | 1827 | 11.30[d] |
| 13 | 29.0 | B | 2.9 | 20 | 1717 | 11.45[d] |
| 14 | 9.2 | B | 2.9 | 20 | 1877 | 13.19[d] |
| 15 | 20.9 | A | 1.2 | 150 | 1759 | 12.90 |
| 16 | <5.0 | B | 1.4 | 135 | 1775 | 12.86 |
| 17 | 23.0 | A | 4.5 | 210 | 1718 | 12.83 |
| 18 | 27.3 | A | 1.5 | 90 | 1726 | 9.53 |
| 19 | 3.0 | A | 1.5 | 90 | 1895 | 11.37 |
| 20 | 9.4 | B | 2.6 | 45 | 1681 | 10.84[e] |
| 21 | 6.2 | B | 2.0 | 90 | 1681 | 9.10 [e] |
| 22 | 2.9 | B | 2.6 | 45 | 1681 | 13.74[e] |
| 23 | 12.5 | B | 2.0 | 90 | 1805 | 10.09 |
| 24 | 8.4 | A | 1.5 | 90 | 1661 | 8.68 |
| 25 | 2.4 | A | 1.5 | 90 | 1661 | 9.05 |
| 26 | 16.3 | A | 1.6 | 150 | 1737 | 10.68 |
| 34 | 11.4 | B | 3.2 | 50 | 1661 | 8.97 |
| 42 | 7.8 | A | 2.9 | 90 | 1731 | 11.96 |
| 43 | 9.6 | A | 1.68 | 90 | 1695 | 9.04 |
| 44 | 4.0 | A | 1.68 | 90 | 1695 | 9.24 |
| 45 | 15.2 | A | 1.5 | 150 | 1771 | 10.72 |
| 46 | 2.3 | A | 1.5 | 150 | 1771 | 10.27 |
| 47 | 4.6 | A | 2.0 | 90 | 1951 | 12.88 |
| 48 | 5.1 | B | 1.3 | 90[c] | 1709 | 9.65 |
| 49 | 3.1 | B | 1.3 | 90[c] | 1709 | 10.51 |
| 50 | 11.9 | B | 2.5 | 25[c] | 1827 | 11.87 |
| 51 | 20.3 | B | 3.6 | 50 | 1681 | 8.48 |
| 52 | 4.5 | B | 3.4 | 40 | 1681 | 8.66 |
| 53 | 2.7 | B | 3.4 | 40 | 1771 | 9.52 |

TABLE VIII-continued

Method of Synthesis and Physical Characteristics

| Compound No. | Yield (%) | Method | Reagent[a] (Equiv.) | Rxn. Time[b] (min.) | FAB-MS (M + H) | $t_R$ (min.) |
|---|---|---|---|---|---|---|
| 54 | 8.2 | A | 1.2 | 120 | 1793 | 12.67 |
| 55 | 16.7 | A | 1.5 | 135 | 1809 | 12.61 |
| 56 | 7.8 | A | 1.3 | 90 | 1752 | 8.75 |
| 57 | 17.4 | A | 12.0 | 60 | 1913 | 10.14 |
| 58 | 31.7 | A | 1.6 | 90 | 1760 | 9.71 |
| 59 | 4.1 | A | 1.6 | 90 | 1928 | 11.47 |
| 60 | 20.3 | A | 2.1 | 105 | 1715 | 9.58 |
| 61 | 20.2 | A | 2.1 | 105 | 1839 | 11.09 |
| 62 | 35.9 | A | 2.34 | 70 | 1715 | 9.27 |
| 63 | 7.7 | A | 2.34 | 70 | 1839 | 10.56 |
| 64 | 11.0 | A | 2.36 | 105 | 1715 | 9.64 |
| 65 | 7.1 | A | 2.36 | 105 | 1839 | 11.34 |
| 66 | 4.7 | A | 2.4 | 105 | 1699 | 11.02[e] |
| 67 | 7.4 | A | 2.4 | 105 | 1699 | 10.79[e] |
| 68 | 2.1 | A | 2.4 | 105 | 1807 | 13.32[e] |
| 70 | 13.0 | B | 4.0 | 60 | 1504 | 10.90[f] |
| 71 | 5.6 | B | 2.9 | 120 | 1484 | 9.43 |
| 72 | 11.7 | B | 2.9 | 120 | 1554 | 11.23 |
| 73 | 19.6 | B | 2.9 | 20 | 1341 | 13.22[f] |
| 74 | 5.0 | B | 3.3 | 45 | 1321 | 10.97 |
| 75 | 17.2 | B | 3.3 | 45 | 1391 | 12.77 |
| 79 | 27.6 | B | 3.6 | 120 | 1376 | 14.11 |
| 76 | 59.4 | B | 4.8 | 90 | 1538 | 12.35 |
| 77 | 10.8 | B | 3.6 | 30 | 1518 | 9.53 |
| 78 | 28.9 | B | 3.6 | 30 | 1588 | 11.32 |

[a]Molar equivalents of aldehyde relative to the glycopeptide
[b]Reaction time, reactions carried out at 50° C. to 70° C. except where indicated.
[c]Reactions carried out at room temperature.
[d]Elution with a 15 min. linear gradient of 10% acetonitrile/0.2% aqueous triethylamine phosphate (pH 3) to 80% acetonitrile/0.2% aqueous triethylamine phosphate (pH 3).
[e]Elution with a 25 min. linear gradient of 5% acetonitrile/0.2% aqueous triethylamine phosphate (pH 3) to 80% acetonitrile/0.2% aqueous triethylamine phosphate (pH 3).
[f]Elution with a 15 min. linear gradient of 5% acetonitrile/0.2% aqueous triethylamine phosphate (pH 3) to 50% acetonitrile/0.2% aqueous triethylamine phosphate (pH 3).

TABLE IX

Method of Synthesis and Physical Characteristics

| Compound No. | Yield (%) | Method | Reagent[a] Equiv. | Time[b] (min.) | FAB-MS (M + H) | $t_R$ (min.) |
|---|---|---|---|---|---|---|
| 27 | 3.5 | D | 7.5 | 60[c] | 1669 | 11.41 |
| 28 | 3.7 | C | 3.5 | 120 | 1689 | 10.88 |
| 29 | 3.3 | C | 3.5 | 120 | 1689 | 11.47 |
| 30 | 11.0 | C | 3.7 | 180 | 1627 | 9.17 |
| 31 | 2.7 | C | 2.3 | 270 | 1627 | 9.83 |
| 32 | 5.3 | C | 3.7 | 180 | 1627 | 10.02 |
| 33 | 3.4 | C | 3.7 | 180 | 1697 | 11.02 |
| 69 | 3.6 | A | 6.0 | 300–360[d] | 1703 | 11.19 |

[a]Molar equivalents of activated ester relative to the glycopeptide.
[b]Reaction time; reactions were carried out at 60° C. to 70° C. except where indicated.
[c]Reaction carried out at 80° C.
[d]Reaction carried out at 100° C.

EXAMPLE 6

Capsule Formulation

Capsules containing 250 mg of Compound 38 are prepared using the following ingredients:

| Ingredient | Weight |
|---|---|
| Compound 38 HCl salt | 255.4 mg |
| Corn starch flowable powder | 150 mg |
| Corn starch | 144.6 mg |

Compound 38 (HCl salt form, 255.4 mg), corn starch flowable powder (150 mg) and corn starch (144.6 mg) are blended in a suitable mixer until homogeneous. The mixture is used to fill a hard gelatin capsule to a net fill weight of 550 mg.

EXAMPLE 7

Suspension Formulation

A sterile insoluble form of Compound 38 is milled or screened to a particle size suitable for suspension. This particulate material is suspended in the following vehicle:

| Ingredient | Weight |
|---|---|
| Lecithin | 1% |
| Sodium citrate | 2% |
| Propylparaben | 0.015% |
| Distilled water | q.s. to desired volume |

EXAMPLE 8

Tablet Formulation

Tablets containing 250 mg of compound 38 are prepared with the following composition:

| Ingredient | Weight |
|---|---|
| Compound 38 HCl salt | 255.4 mg |
| Microcrystalline cellulose | 101.1 mg |
| Croscarmellose sodium | 12.0 mg |
| Povidone | 12.0 mg |
| Magnesium stearate | 3.0 mg |
| Stearic acid | 4.0 mg |
| Purified water | 0.16 ml |

We claim:
1. A compound of the formula I

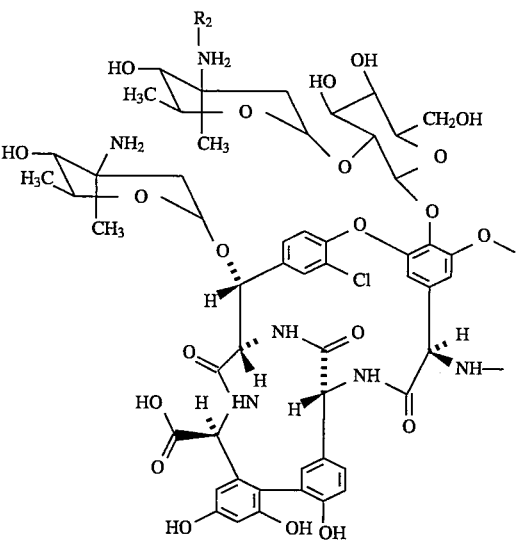

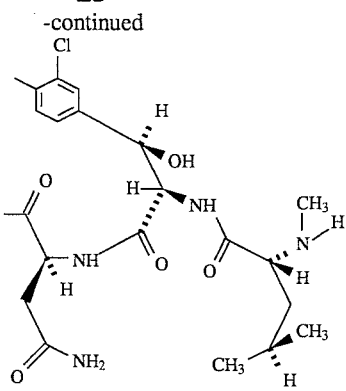

$R_2$ is $C_8$–$C_{12}$ alkyl or a group of formula

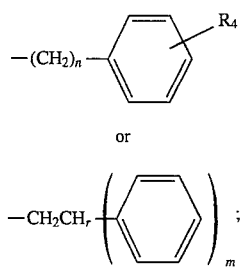

or

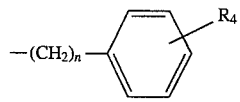

wherein n is 1 to 3;
$R_4$ is hydrogen, halo, $C_1$–$C_8$ alkyl, or $C_1$–$C_8$ alkoxy;
m is 2 or 3 and r=3-m;
or a pharmaceutically acceptable salt thereof.

2. A compound of claim 1 wherein $R_2$ is $C_8$–$C_{12}$ alkyl.
3. A compound of claim 2 wherein $R_2$ is octyl.
4. A compound of claim 2 wherein $R_2$ is decyl.
5. A compound of claim 1 wherein $R_2$ is

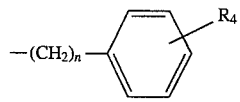

6. A compound of claim 5 wherein $R_2$ is phenylethyl, diphenylethyl, phenylpropyl, benzyl, 4-octylbenzyl, 4-octyloxybenzyl, p-bromobenzyl, p-chlorobenzyl, o-chlorobenzyl, m-chlorobenzyl, or p-fluorobenzyl.
7. A compound of claim 6 wherein $R_2$ is p-chlorobenzyl.
8. A compound of claim 6 wherein $R_2$ is p-bromobenzyl.
9. A composition useful for the control of susceptible bacterial infections comprising an effective amount of a compound of claim 1 and a suitable pharmaceutical vehicle.
10. A composition useful for the control of susceptible bacterial infections comprising an effective amount of a compound of claim 2 and a suitable pharmaceutical vehicle.
11. A composition useful for the control of susceptible bacterial infections comprising an effective amount of a compound of claim 3 and a suitable pharmaceutical vehicle.
12. A composition useful for the control of susceptible bacterial infections comprising an effective amount of a compound of claim 4 and a suitable pharmaceutical vehicle.
13. A composition useful for the control of susceptible bacterial infections comprising an effective amount of a compound of claim 5 and a suitable pharmaceutical vehicle.
14. A composition useful for the control of susceptible bacterial infections comprising an effective amount of a compound of claim 6 and a suitable pharmaceutical vehicle.
15. A composition useful for the control of susceptible bacterial infections comprising an effective amount of a compound of claim 7 and a suitable pharmaceutical vehicle.
16. A composition useful for the control of susceptible bacterial infections comprising an effective amount of a compound of claim 8 and a suitable pharmaceutical vehicle.
17. A method for treating susceptible bacterial infections which comprises administering an effective amount of a composition of claim 9 to an animal.
18. A method for treating susceptible bacterial infections which comprises administering an effective amount of a composition of claim 10 to an animal.
19. A method for treating susceptible bacterial infections which comprises administering an effective amount of a composition of claim 11 for an animal.
20. A method for treating susceptible bacterial infections which comprises administering an effective amount of a composition of claim 12 to an animal.
21. A method for treating susceptible bacterial infections which comprises administering an effective amount of a composition of claim 13 to an animal.
22. A method for treating susceptible bacterial infections which comprises administering an effective amount of a composition of claim 14 to an animal.
23. A method for treating susceptible bacterial infections which comprises administering an effective amount of a composition of claim 15 to an animal.
24. A method for treating susceptible bacterial infections which comprises administering an effective amount of a composition of claim 16 to an animal.
25. A method for treating a bacterial infection due to a vancomycin-resistant enterococcus which comprises administering an effective amount of a composition of claim 9 to an animal.
26. A method for treating a bacterial infection due to a vancomycin-resistant enterococcus which comprises administering an effective amount of a composition of claims 10 to an animal.
27. A method for treating a bacterial infection due to a vancomycin-resisting enterococcus which comprises administering an effective amount of a composition of claim 11 to an animal.
28. A method for treating a bacterial infection due to a vancomycin-resistant enterococcus which comprises administering an effective amount of a composition of claim 12 to an animal.
29. A method for treating a bacterial infection due to a vancomycin-resistant enterococcus which comprises administering an effective amount of a composition of claim 13 to an animal.
30. A method for treating a bacterial infection due to a vancomycin-resistant enterococcus which comprises administering an effective amount of a composition of claim 14 to an animal.
31. A method for treatment a bacterial infection due to a vancomycin-resistant enterococcus which comprises administering an effective amount of a composition of claim 15 to an animal.
32. A method for treating a bacterial infection due to a vancomycin-resistant enterococcus which comprises administering an effective amount of a composition of claim 16 to an animal.

* * * * *